(12) United States Patent
Kyotani et al.

(10) Patent No.: US 6,561,806 B2
(45) Date of Patent: May 13, 2003

(54) DENTAL MAGNETIC ATTACHMENT

(75) Inventors: Ikuo Kyotani, Tokyo (JP); Osamu Kujirai, Tokyo (JP); Mitsuo Hata, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 10/004,887

(22) Filed: Dec. 7, 2001

(65) Prior Publication Data
US 2002/0115041 A1 Aug. 22, 2002

(30) Foreign Application Priority Data
Dec. 20, 2000 (JP) ........................................ 2000-387635

(51) Int. Cl.⁷ ............................................. A61C 13/235
(52) U.S. Cl. ........................................................ 433/189
(58) Field of Search .......................................... 433/189

(56) References Cited

FOREIGN PATENT DOCUMENTS

| JP | 1-303145 | 12/1989 |
|---|---|---|
| JP | 4-54958 | 2/1992 |

*Primary Examiner*—Cary E. O'Connor
(74) *Attorney, Agent, or Firm*—Oblon, Spivak, McClelland, Maier & Neustadt, P.C.

(57) ABSTRACT

To develop a dental magnetic attachment having stable adhesive properties and capable of being adhered and fixed in a position in an alveolar ridge side, which does not require one to perform sandblast processing during the use and does not form a space between a permanent magnet structure and a denture base even when it is used in an oral cavity over a long period of time. 80 to 100% of a surface of a cover as a shell of the permanent magnet structure of the dental magnetic attachment, except for a surface thereof coming contact with a keeper, is beforehand processed by a chemical or mechanical method so as to have a surface roughness such that a maximum roughness, Rmax is 5 to 15 μm and that a ten-point average roughness, Rz is 3 to 8 μm.

1 Claim, 1 Drawing Sheet

DENTAL MAGNETIC ATTACHMENT

BACKGROUND OF THE INVENTION

1. Field of the Invention

The present invention relates to a dental magnetic attachment utilizing amagnetic attraction force. More particularly, the present invention relates to a dental magnetic attachment in which a surface of a shell of a permanent magnet structure to be adhered and fixed to an alveolar ridge side of a denture base is beforehand processed so as to have a prescribed roughness, thereby enabling one to adhere and fix the permanent magnet structure within the denture base, with a stable holding power.

2. Description of the Conventional Art

As a method for setting a partial or complete denture within an oral cavity, in recent years, employed is a method utilizing a magnetic attraction force acting between a permanent magnet and a soft magnetic material. That is, this method is a method in which a keeper made of a soft magneticmaterial is fixedly set in an alveolar ridge portion within an oral cavity, whereas a permanent magnet structure is adhered and fixed in a position opposite to the keeper in an alveolar ridge side of a denture base, thereby enabling one to set a denture utilizing a magnetic attraction force acting between the keeper and the permanent magnet structure. According to this method, not only the denture can be set within the oral cavity without any hindrance in the function and esthetics of the denture, but also placement and removal to be carried out for the purpose of cleaning up the denture and the like are easy. Thus, application examples thereof are increasing rapidly.

In general, the setting of the denture using such a dental magnetic attachment is carried out in the following manner. That is, a root member of a keeper, which is fixedly set on a back surface of a flat plate made of a soft magnetic material positioning inside an oral cavity, by means of casting to embedded alloys or other methods, the keeper being formed so as to have a longitudinal section in an approximately T-shape, is embedded and fixedly set within a tooth root or artificial tooth root of residual teeth in an alveolar ridge portion in the oral cavity; a permanent magnet structure is adhered and fixed in a hole provided in a denture base positioning opposite to the keeper, by an adhesive or a self-curing resin, in the alveolar ridge side of the denture base; and during setting a denture within the oral cavity, a magnetic attraction force acts between the keeper and the permanent magnet to set the denture such that it is not dropped easily, while during the removal, it can be easily taken out by applying a larger power then the magnetic attraction force.

As the permanent magnetic structure of the dental magnetic attachment to be used in such a way, employed are generally those which accommodated a permanent magnet within the inside, the surrounding thereof being covered by a shell made of a corrosion-resistant soft magnetic or non-magnetic metal. In order to set the denture stably, the metal material that is used for the shell is required to have superior corrosion resistance for resisting to the corrosion in an environment within the oral cavity. Accordingly, in general, as the corrosion-resistant soft magnetic material, employed are ferrite-based stainless steels such as 16 ~18Cr —bal Fe (SUS430), 17~20Cr—1.75~2.5Mo-bal Fe (SUS444), and 28.5~32.0Cr—1.5~2.5Mo—bal Fe (SUS447J1), and austenite-based stainless steels represented by SUS316L. And, exemplified are those in which the corrosion-resistant metal material covers the permanent magnet structure except for a surface thereof coming contact with the keeper, or the whole surface of the permanent magnet structure in a thickness such that the magnetic attraction force between the permanent magnet structure and the keeper is not influenced.

The permanent magnet structure of the dental magnetic attachment is limited in terms of the size because it is adhered within the denture base. In general, a pillar having a diameter of about 3 to 4 mm and a height of about 1.5 to 2 mm, or an approximately square pillar having one side of about 2 to 3 mm and another side of about 3 to 4 mm and having a height of about 1.5 to 2 mm, is formed, and then adhered and fixed for use in a hole provided in the alveolar ridge side of the denture base of the completed denture. In this case, the works at the dental clinical or dental laboratories are often carried out in an environment where saliva or sebum from fingers, or other substances lowering the adhesive capacity are readily attached to the surface of the permanent magnet structure. In the case where the adhesion works to the denture base are carried out in the state that foreign matters are attached to the surface of the permanent magnet structure, the adhesive strength between the permanent magnet structure and the denture base is markedly lowered, leading to formation of a space between the permanent magnet structure and the denture base. In this case, when the space is large, the saliva or remnants of food or the like invade into the space, resulting in a hygienic problem. As the case may be, the permanent magnet structure is corroded. In a more severe case, there occurs a problem that the permanent magnet structure is dropped from the denture base.

This is considered to occur by the following matter. That is, the denture is used under severe conditions such as a condition under which a large stress is repeatedly applied to a part of the denture base by mastication, or a condition under which the denture is influenced directly by a temperature difference due to the contact with foods and drinks. Accordingly, the space is gradually formed during the use over a long period of time, and hence, the above-described problem is inevitable from occurrence.

Thus, as means for improving the adhesive strength, the manufactures give instructions to dentists or dental technicians to carry out the operation such that the surface of the permanent magnet structure must be surely cleaned during the adhesion; and in order to make the adhesive or self-curing resin easy to attach to the surface of the shell, after sandblast processing, the surface of the shell is subjected to primer processing and then adhered with the adhesive or self-curing resin. As means for preventing the dropping, with respect to the permanent magnet structure, there are applied various improvements for imparting mechanical retention forms such as protrusions or grooves to the side surface of the shell, as disclosed in Japanese Patent Laid-Open Nos. 54958/1992 and 150156/1996.

By taking these means, not only the improvement in adhesive properties of the permanent magnet structure to the denture base is devised, but also the permanent magnet structure is less dropped from the denture base due to the mechanical retention. However, as described above, for a dentist or a dental technician, uniform sandblast processing of an extremely small permanent magnet structure is a difficult to perform and a complicated operation requiring a skill. In the case where the sandblast processing is insufficient, a satisfactory effect for improving the adhesive properties is not likely attained sufficiently. On the other hand, when the sandblast processing is carried out excessively, the shell is likely bored, resulting in a problem such that the permanent magnet is exposed. In addition, there is a problem that a dentist or a dental technician who does not have a sandblast-processing unit cannot perform such processing.

SUMMARY OF THE INVENTION

Thus, the present invention is aimed to develop a dental magnetic attachment having a stable adhesive capacity, which does not require a dentist or a dental technician to perform sandblast processing during the use and does not form a space between a permanent magnet structure and a denture base even when it is used in an oral cavity over a long period of time, by beforehand processing a surface of a shell of the permanent magnet structure to be adhered and fixed to an alveolar ridge side of the denture base so as to have a roughness at which an adhesive strength can be most effectively enhanced.

In order to achieve the above-described aim, we, the present inventors made extensive and intensive investigations. As a result, it has been found that in the case where a surface of a shell of a permanent magnet structure except for a surface thereof coming contact with a keeper is beforehand processed by a chemical or physical method so as to have a surface roughness such that a maximum roughness is 5 to 15 $\mu$m and that a ten-point average roughness is 3 to 8 $\mu$m, a primer surely penetrates into irregularities formed on the surface, so that the metal surface is activated; a chemical bond between the metal surface and an adhesive to be applied thereafter is effectively brought, thereby enabling to impart a stable adhesive strength; and the irregularities formed on the surface act effectively to enhance a mechanical retention force, leading to accomplishment of the present invention.

Specifically, the dental magnetic attachment according to the present invention is a dental magnetic attachment, which comprises a keeper comprising a soft magnetic material to be fixedly set in an alveolar ridge portion within an oral cavity; and a permanent magnet structure having a permanent magnet aligned inside a shell to be adhered and fixed in a position of an alveolar ridge side of a denture base opposite to the keeper, wherein 80 to 100% of a surface of the shell of the permanent magnet structure except for a surface thereof coming contact with the keeper has a surface roughness such that a maximum roughness, Rmax is 5 to 15 $\mu$m and that a ten-point average roughness, Rz is 3 to 8 $\mu$m.

DESCRIPTION OF THE PREFERRED EMBODIMENTS

The permanent magnet structure of the dental magnetic attachment according to the present invention will be described below in detail with reference to the drawings.

Figure 1:
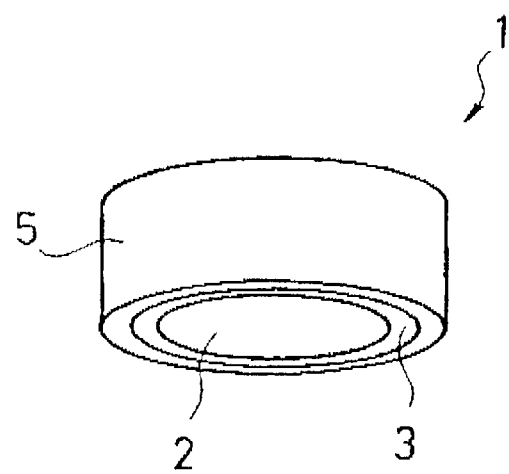
FIG. 1 is a perspective view showing a cup yoke type permanent magnet structure, which is a representative example of a permanent magnet structure of a dental magnetic attachment according to the present invention.
Figure 2:
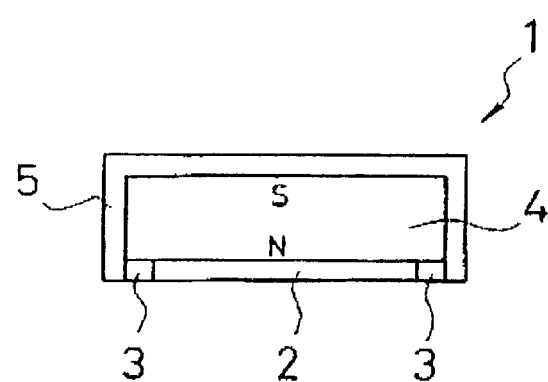
FIG. 2 is a cross-sectional explanatory view of the permanent magnet structure of the dental magnetic attachment shown in FIG. 1.
Figure 3:
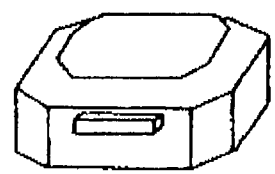
FIG. 3 is a perspective view showing a shape of a shell of another embodiment of the permanent magnet structure of the dental magnetic attachment according to the present invention.
Figure 4:
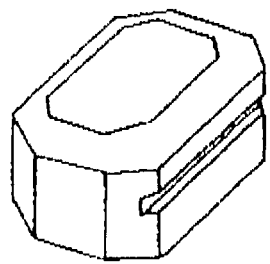
FIG. 4 is a perspective view showing a shape of a shell of a still another embodiment of the permanent magnet structure of the dental magnetic attachment according to the present invention.

FIG. 1 is a perspective view showing a cup yoke type permanent magnet structure, which is a representative example of a permanent magnet structure of a dental magnetic attachment according to the present invention; FIG. 2 is a cross-sectional explanatory view of the permanent magnet structure of the dental magnetic attachment shown in FIG. 1; FIG. 3 is a perspective view showing a shape of a shell of another embodiment of the permanent magnet structure of the dental magnetic attachment according to the present invention; and FIG. 4 is a perspective view showing a shape of a shell of a still another embodiment of the permanent magnet structure of the dental magnetic attachment according to the present invention.

In a cup yoke type permanent magnet structure 1 as shown in FIGS. 1 and 2, which is a representative example, in a lower side of a permanent magnet 4 (e.g., NdFeB) having N and S poles in the vertical direction, as shown in FIG. 2, aligned is a spacer 3 made of an austenite-based stainless steel (e.g., SUS316L) surrounding a disc 2 made of a soft magnetic stainless steel (e.g., SUS444) in the center thereof, to form a magnetic circuit, thereby enhancing an adsorptive force. Further, an outer periphery except for the surfaces of the permanent magnet 4, the disc 2 and the spacer 3 coming into contact with a keeper is covered by a cover 5 which is formed in a closed-end cylinder shape, made of a soft magnetic stainless steel (e.g., SUS444), and used as a shell.

The permanent magnet structure 1 of the dental magnetic attachment is processed so as to have a surface roughness such that 80 to 100% of the surface of the cover 5 as a shell thereof except for the surface coming into contact with the keeper (a surface where the disc 2 and the spacer 3 are exposed) has a maximum roughness (Rmax) of 5 to 15 $\mu$m and a ten-point average roughness (Rz) of 3 to 8 $\mu$m. In the case where the maximum roughness (Rmax) is less than 5 $\mu$m, the irregularities are too small, so that an effect for keeping a mechanical retention force is low. On the other hand, in the case where it exceeds 15 $\mu$m, not only a primer or an adhesive tends to hardly penetrate into a deepest part of a concave portion, but also it becomes necessary to increase the thickness of the cover 5 as the shell. Thus, such is not suitable. Further, in the case where the ten-point average roughness (Rz) is less than 3 $\mu$m, the effect for roughing the surface is low, so that an effect for enhancing the adhesive strength is insufficient. On the other hand, in the case where it exceeds 8 $\mu$m, since the primer that has penetrated into the concave portion is liable to retain, the adhesive strength tends to be lowered. Thus, such is not suitable. The above-described surface processing is applied to 80 to 100% of the surface of the cover 5 as the shell, except for the surface thereof coming into contact with the keeper. When 80% or more of the surface is processed, the prescribed effect can be attained. But, since a side surface portion is a portion where a space is most likely formed, it is preferred to subject the side surface portion to the processing preferentially. Incidentally, since the magnetic adsorptive force of the surface coming into contact with the keeper is possibly lowered, the above-described surface processing should not be applied to this surface coming into contact with the keeper.

The permanent magnet structure that is used for the dental magnetic attachment according to the present invention does not differ at all in terms of the structure, shape, etc. from permanent magnet structures that have hitherto been generally used, except for the matter that the shell surface thereof is processed so as to have a prescribed surface roughness. Specifically, in addition to the cup yoke type permanent magnet structure as shown in FIGS. 1 and 2, which is a representative example, employable are any permanent magnetic structures of a sandwich type, a split ball type, etc. With respect to the appearance shape, not only a pillar-like shape as shown in FIGS. 1 and 2 but also a square pillar-like shape are employable. Further, employable are also any of other structures and shapes, such as a shape as shown in FIG. 3, in which a protrusion is provided in a side surface portion of the shell, and a shape as shown in FIG. 4, in which a concave portion is provided in a side surface portion of the shell. Moreover, with respect to the method for processing the shell surface so as to have a prescribed surface roughness, there are no particular restrictions so far as the prescribed surface roughness is obtained. The surface processing can be achieved by various known processing methods including sandblast processing, barrel polishing processing, emboss processing, and chemical corrosion processing. These processing methods may be carried out singly or in combination.

The permanent magnet structure having such surface properties for the dental magnetic attachment according to the invention, is used upon being adhered and fixed in the alveolar ridge side of the denture base, likewise the conventional permanent magnet structures for the dental magnetic attachment. During the use, a permanent magnet structure having a proper size is chosen, a surface of which is cleaned, if necessary. Then, the permanent magnet structure is subjected to primer processing and embedded within the denture base using, e.g., an adhesive or a self-curing resin, whereby it is adhered and fixed within the denture base. But, the permanent magnet structure used for the dental magnetic attachment according to the present invention is beforehand processed so as to have surface properties suitable for the adhesion. Accordingly, a dentist or a dental technician can surely adhere and fix the permanent magnet structure within the denture base with a high adhesive force, even when the troublesome sandblast processing is not carried out during the use.

EXAMPLES 1 TO 3 AND COMPARATIVE EXAMPLE 1

In order to evaluate the performance of the permanent magnet structure used for the dental magnetic attachment, the surface of the permanent magnet structure for denture base attachment having the shape as shown in FIG. 1, except for the surface coming into contact with a keeper was subjected to various surface processing methods as shown in Table 1 and then to measurement of an adhesive strength and observation of a fractured surface as well as test of a space formation by thermal fatigue.

Measurement of Adhesive Strength and Observation of Fractured Surface

In a central portion of one end of a resin block (15 mm×15 mm×30 mm) made of a denture base resin (a trade name: GC Acron, made by GC Corporation), adhered and fixed was a surface of a permanent magnet structure (4 mm in diameter×2 mm in thickness) having subjected to the surface processing of various methods as shown in Table 1, the surface being that in the opposite side to a surface coming into contact with a keeper using a self-curing resin (a trade name: GC Uni Fast II, made by GC Corporation), after processing of the surface with a metal surface-processing agent (a trade name: GC Metal Primer II, made by GC Corporation). The resulting attachment was immersed in water at 4° C. and warm water at 60° C. alternately 2,000 times for one minute for each time. Thereafter, a tensile test jig was installed on the surface of the permanent magnet structure in the keeper side, and the tensile test was carried out to measure the adhesive strength. Further, the fractured surface was evaluated through microscopic observation. The test results are summarized and shown in Table 1.

Test of Space-formation by Thermal Fatigue

In a central portion of a resin block (15 mm×15 mm×10 mm) made of a denture base resin (a trade name: GC Acron, made by GC Corporation), provided was a hole having a diameter of 4.5 mm and a depth of 2.5 mm. Into this hole, adhered and fixed was a permanent magnet structure (4 mm in diameter×2 mm in thickness) having subjected to the surface processing of various methods as shown in Table 1, using a self-curing resin (a trade name: GC Uni Fast II, made by GC Corporation), after processing with a metal surface-processing agent (a trade name: GC Metal Primer II, made by GC Corporation) The resulting attachment was immersed in water at 4° C. and warm water at 60° C. alternately 20,000 times for one minute for each time. Thereafter, the attachment was immersed in a fuchsine solution, thereby confirming the presence or absence of the formation of a space(s) on the adhered and fixed surface of the permanent magnet structure. Incidentally, the test was carried out with respect to ten samples. The results about the number of formed spaces are shown in Table 1.

TABLE 1

| | Surface processing | Adhesive strength | State of fractured surface | Formation of space(s) |
|---|---|---|---|---|
| Example 1 | Sandblast processing Rmax: 8.2 μm, Rz: 4.0 μm 95% of the shell except for the keeper side | 68 MPa | Adhesive was fractured | 0 |
| Example 2 | Sandblast processing Rmax: 10.8 μm, Rz: 5.3 μm 100% of the shell except for the keeper side | 74 MPa | Adhesive was fractured | 0 |
| Example 3 | Chemical corrosion processing Rmax: 12.4 μm, Rz: 6.1 μm 90% of the shell except for the keeper side | 72 MPa | Adhesvie was fractured | 0 |
| Comparative Example 1 | Non-processing Rmax: 1.3 μm, Rz: 0.7 μm | 27 MPa | Interface peeling occurred | 10 |

As described above in detail, in the permanent magnet structure for the dental magnetic attachment according to the present invention, the surface to be adhered to the denture base is beforehand processed so as to have surface properties suitable for the adhesion. Accordingly, a dentist or a dental technician can surely adhere and fix the permanent magnet structure within the denture base with a high adhesive strength, even when the troublesome sandblast processing is not carried out during the use. Further, even when the dental magnetic attachment according to the present invention is used within the oral cavity over a long period of time, no space is formed between the permanent magnet structure and the denture base, and stable adhesive properties can be kept. Thus, the dental magnetic attachment according to the present invention is greatly valuable in contributing to the dental remedy.

While the present invention has been described in detail and with reference to specific embodiments thereof, it will be apparent to one skilled in the art that various changes and modifications can be made therein without departing from the spirit and scope thereof.

What is claimed is:

1. A dental magnetic attachment comprising:

a keeper composed of a soft magnetic material to be fixedly set in an alveolar ridge portion within an oral cavity; and a permanent magnet structure having a permanent magnet aligned inside a shell to be adhered and fixed in a position of an alveolar ridge side of a denture base opposite to the keeper, wherein 80 to 100% of a surface of the shell of the permanent magnet structure except for a surface thereof coming into contact with the keeper, has a surface roughness such that a maximum roughness, Rmax, is 5 to 15 $\mu$m and a ten-point average roughness, Rz, is 3 to 8 $\mu$m.

* * * * *